United States Patent [19]

Hebborn

[11] 4,102,995

[45] Jul. 25, 1978

[54] TAR GEL FORMULATION

[75] Inventor: Peter Hebborn, Clarence, N.Y.

[73] Assignee: Westwood Pharmaceuticals Inc., Buffalo, N.Y.

[21] Appl. No.: 685,844

[22] Filed: May 13, 1976

[51] Int. Cl.² .............................................. A61K 31/78
[52] U.S. Cl. ...................................... 424/81; 424/167; 424/177; 424/230; 424/355
[58] Field of Search .................. 424/81, 196, 167, 355

[56] References Cited

U.S. PATENT DOCUMENTS

| | | | |
|---|---|---|---|
| 2,602,039 | 7/1952 | Wershaw | 424/167 |
| 2,622,057 | 12/1952 | Augenblick | 424/167 |
| 2,798,053 | 7/1957 | Brown | 424/57 |
| 3,043,745 | 7/1962 | Singer | 424/167 |
| 3,061,512 | 10/1962 | Anderson et al. | 424/167 |
| 3,071,510 | 1/1963 | Wershaw et al. | 424/167 |
| 3,210,251 | 10/1965 | King | 424/70 |
| 3,262,851 | 7/1966 | Gottfried et al. | 424/267 |
| 3,472,931 | 10/1969 | Stoughton | 424/60 |
| 3,485,915 | 12/1969 | Gerstein et al. | 424/60 |
| 3,627,871 | 12/1971 | Groves et al. | 424/78 |
| 3,749,773 | 7/1973 | Ninger et al. | 424/81 |

OTHER PUBLICATIONS

Lemberger, Handbook on Non-Prescription Drugs, (1973); pp. 161–166.
Lubowe, Ibid, pp. 167–171.

Primary Examiner—Leonard Schenkman
Attorney, Agent, or Firm—Irving Holtzman; David J. Mugford

[57] ABSTRACT

A tar formulation used in the treatment of skin disorders containing tar, propylene glycol, ethyl alcohol and a gelling agent e.g. Carbopol 940.

12 Claims, No Drawings

TAR GEL FORMULATION

This invention relates to tar preparations useful in the treatment of skin disorders. More particularly, it concerns compositions containing coal tar that are especially suitable as adjuncts in the treatment of skin conditions such as psoriasis, chronic atopic dermatitis, lichen simplex chronicus, nummular eczema, etc.

Crude coal tar is a well-known by-product of the destructive distillation of coal. It contains approximately 400 chemical components including benzene, toluene, naphthalene, anthracene, xylene and other aromatic hydrocarbons; phenol, cresol, and other phenolic bodies; ammonia, pyridine, and other organic bases. It has a long history and wide acceptance in the treatment of many skin disorders, although the precise biochemical mechanism of its therapeutic action is not conclusively known. Because of many years of empirical evidence of tar's benefits, however, it is considered a classical remedy in dermatology, and has long been used in lotions, shampoos, and bath oils, as well as in ointments.

Some of the therapeutic dermatologic effects of tar, and the constituents that are thought to be responsible for producing them, include the following:

(1) Antipruritic and antibacterial: phenols, cresol, and naphthalene;
(2) Keratoplastic (normalizing the production of keratin): methylnaphthalene, dinaphthalene, xylenol, and naphthol;
(3) Photosensitizing: acridine compounds in the anthracene oil fraction. Coal tar is credited with exerting an inhibitory action on the pentose cycle in cellular metabolism, which is particularly active in psoriasis. As a result, there is a reduction in the activity of the enzymes G6PD and NADP. This inhibitory action is said to reduce DNA and RNA synthesis, resulting in the inhibition of mitotic activity and protein syntheis. A reduction of mitosis, or cell division, is beneficial to the psoriatic patient because one of the prime factors in the pathology or psoriasis is an extremely accelerated proliferation of the epidermis.

One of the most strikingly effective treatments for psoriasis involves the application of a tar composition followed by exposure to ultraviolet light. The combination of these two modes of therapy produces a heightened, synergistic effect, which cannot be achieved by either alone. The tar sensitizes the skin, with the result that UV radiation is more effective, and the UV rays apparently oxidize constituents of the tar that have penetrated the skin, which may accelerate the therapeutic action of the tar.

A variety of coal tar preparations have been suggested in the prior art for use in the treatment of skin conditions such as psoriasis and eczema. These have taken the forms of lotions, liquids, creams, ointments, shampoos and gels containing varying amounts of coal tar. Typical of the commercial compositions that are available are those described in the "Handbook of Non-Prescription Drugs" 1969 Edition, edited by G. B. Griffenbager pages 122–126. One of the coal tar gel preparations that is available commercially contains a combination of 5% crude coal tar extract and 2% allanton in a gel base. In addition, several patents have been granted over the years relating to the incorporation of coal tar in a variety of carriers. In this connection, attention is directed to the following: U.S. Pat. Nos. 3,627,871; 3,472,931; 3,043,745; 3,061,512; 3,071,510; 3,262,851; 2,622,057; and 2,602,039.

However, the prior art commercial compositions that are available have several disadvantages. Thus, for example, the gel product referred to above does not adequately penetrate the skin. Consequently, its action is not long lasting and it does not sufficiently resist the effects of bathing. Moreover, the degree to which it stains fabrics is hardly acceptable. In addition, it lacks adequate cosmetic acceptability. This later disadvantage is also generally characteristic of the other commercially available coal tar products.

It has now been found that superior tar products can be provided that are useful as adjuncts in the treatment of a number of skin disorders by incorporating the tar, in pharmaceutically active amounts, in a system also containing ethanol and propylene glycol. In their preferred form, the present compositions take the shape of a stable cosmetically acceptable gel as described in more detail below. These compositions avoid the many disadvantages noted above that are encountered in prior art tar products that are used for these purposes.

U.S. Pat. No. 3,749,773 suggests the preparation of a topical ointment of betamethasone-17-benzoate in a vehicle comprising a mixture of ethanol and propylene glycol. This patent further suggests that this product may be gelled with a neutralized Carbopol 940. Although the patentees make some vague and general reference to steroids, it seems clear that nothing of a concrete nature is suggested as having application to their invention excepting betamethasone 17-benzoate.

Moreover, it is also clear that this patent seeks to solve a specific problem; namely, providing an ointment base in which the ordinarily difficult to incorporate steroid is soluble. However, there is nothing in this reference which suggests the use of the base disclosed therein as a vehicle for the tars which is characteristic of the present invention. The steroids of U.S. Pat. No. 3,749,733 are quite remote from the active components of tars as described above. Moreover, there is nothing in U.S. Pat. No. 3,749,733 which suggests that the incorporation of a tar in a base containing propylene glycol, ethyl alcohol and a gelling agent in accordance with the present invention would give the superior results discussed in more detail below when compared with typical prior art tar preparations.

The nature of the tar that may be used in formulating compositions of the present invention may vary somewhat. Thus, for example, crude tars such as Coal Tar U.S.P. (*Pix Carbonis*); Pine Tar (*Pix Pini*) or Juniper Tar (*Pix Juniperi*) can be employed for the present purposes. Moreover, tar extracts prepared by extracting a crude coal tar with various solvents may also be used in formulating the compositions of the present invention. Two such extracts are described in Remington's Practice of Pharmacy, 10th Edition, page 730 and are identified as Coal Tar Solution N.F. (Liquid Carbonis Detergens) and Chloroformic Coal Tar Solution N.F. (Liquor Picis Carbonis Chloroformicus). In addition, extracts of crude coal tar with any one or more of the following solvents provide a tar solution or suspension that is useful for the present purposes: isopropyl myristate; PEG-6-Dilaurate; polyoxyethylene(4) lauryl ether; Arlamol-E (Propoxylated(15 moles propylene oxide)-stearyl ether); polyoxyethylene(10) oleyl ether; Procetyl AWS (polypropylene glycol(5) cetyl ether); Standamul HE (glycereth-7-coconate). These extracts are prepared by treating about 40 parts by weight of Crude Coal Tar (U.S.P.) with about 60 parts by weight of the solvent system. These extracts will, in general, contain about 75–80% by weight of the organic solvent soluble ingredients of the Coal Tar (U.S.P.) and will exclude the organic solvent insoluble carbon particles and pitch.

The quantity of tar that will be contained in the compositions of the present invention will vary somewhat. All that is essentially required is that therapeutically effective concentrations of the active ingredients of the tar be contained in the composition. Ordinarily, however, the compositions will contain from about .5% to 15% and preferably from about 1% to 10% by weight based on the total weight of the compositions of tar in the form of crude tar or as an extract thereof.

Essential features of this invention are the propylene glycol and ethyl alcohol that constitute substantial portions of the vehicle of the compositions. These may also be present in varying amounts depending upon other ingredients contained in the compositions and its intended use. Usually, however, the propylene glycol will constitute between about 25% to 65% by weight of the final composition. The ethyl alcohol (on an anhydrous basis) will ordinarily comprise about 20% to 35% by weight based on the total weight of the composition.

Another important component of the present compositions is the gelling agent. These may be selected both as to type and quantity to give products of various viscosities. In the preferred form of this invention, the gelling agent is selected so as to produce an elegantly formed stable gel. A variety of gelling agents may be used for the present purposes. However, preferred gelling agents are the so-called carboxylated vinylic polymers and particularly those disclosed in U.S. Pat. 2,798,053. Among these, those of special interest herein are described generally as interpolymers of a monomeric monoolefinic acrylic acid of the structure:

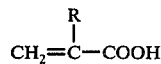

$$CH_2=\overset{R}{\underset{|}{C}}-COOH$$

where R is a substituent selected from the class consisting of hydrogen and lower alkyl groups, and from about 0.1 to about 10% by weight based on the total monomers of a monomeric polyether of an oligosaccharide in which the hydroxyl groups which are modified are etherified with allyl groups said polyether containing at least two allyl ether groups per oligosaccharide molecule.

Commercially available interpolymers of this type are marketed under the trade name Carbopol. These are described as being polymers of acrylic acid cross-linked with about 1% of a polyallyl ether of sucrose having an average of about 5.8 allyl groups for each sucrose molecule. These polymers have molecular weights in the order of magnitude of 1,000,000. Such polymers are available from the B.F. Goodrich Chemical Company and are sold under the trademark "Carbopol 934". Similarly, constituted products are designated "Carbopol 940" and "Carbopol 941".

The various Carbopols are distinguished from each other by the manufacture on the basis of their viscosity. This is given in the Table I below:

| | Brookfield RVF or RVT viscosity, cP (20 rpm. at 25° C, neutralized solutions) | | | |
|---|---|---|---|---|
| | % Sol. | Min. | Max. | Spindle |
| Carbopol 934 | 0.2 | 2,050 | 5,450 | 4 |

-continued

| | Brookfield RVF or RVT viscosity, cP (20 rpm. at 25° C, neutralized solutions) | | | |
|---|---|---|---|---|
| | % Sol. | Min. | Max. | Spindle |
| | 0.5 | 30,500 | 39,400 | 6 |
| Carbopol 940 | 0.2 | 15,000 | 35,000 | 6 |
| | 0.5 | 40,000 | 60,000 | 7 |
| | 1.0 | 50,000 | 85,000 | 7 |
| Carbopol 941 | 0.05 | 700 | 3,000 | 3 |
| | 0.2 | 1,950 | 7,000 | 4 |
| | 0.5 | 4,000 | 11,000 | 5 |

The polymers are gelled by neutralizing them with an alkaline material. Suitable neutralizing agents are the organic amines among which may be mentioned triethanolamine, triethylamine, isopropylamine, diisopropylamine, morpholine, etc.

Another class of preferred gelling agents is the hydroxypropyl cellulose polymers. These are described in U.S. Pat. No. 3,485,915 (Column 1) and U.S. Pat. No. 3,210,251 referred to therein which description is incorporated herein by way of reference. Among the hydroxypropyl cellulose polymers that are useful for the purposes of the present invention and that are available commercially is a product sold under the trade name "Klucel HA". This has a viscosity of between about 1500 and 2500 cps. in a 1% aqueous solution and a viscosity of between about 4000 to 650 cps. in a 2% aqueous solution as determined at 25° C using a Brookfield LVF viscometer.

The quantity of gelling agent that may be contained in the present compositions may also vary somewhat. Ordinarily, this will constitute between 0.5% to 5% by weight and preferably between about 1% to 2% by weight based on the total weight of the finished composition.

The compositions of the present invention will also ordinarily contain substantial aqueous components. When water is present, it may also vary dependent upon the nature of the product desired. Usually, this will constitute between about 5% to 35% and preferably between about 10% and 32% by weight based on the total weight of the finished compositions. It is also preferred to use demineralized water.

It is sometimes advantageous to add additional therapeutically active ingredients to the present compositions which may serve to augment the activity of the tar actives or to supplement them. A variety of materials may be used for this purpose. Of special interest as an auxiliary skin treating agent is the keralytic agent and especially salicylic acid. When these are used, they may be employed over a range of concentration which may vary from about 4% to 8% by weight. However, the preferred concentration of auxiliary keralytic agent e.g. salicylic acid, will be about 6% by weight.

In addition, for purposes of formulating more elegant products, other additives may be incorporated into the present compositions. Typical among these may be emulsifying agents, emollients, perfumes, etc.

The following examples are given to further illustrate the present invention. It is to be understood, however, that the invention is not limited thereto.

A series of tar solutions were first prepared using different tar. The tars employed were Pine Tar, Juniper Tar and Liquor Carbonis Detergens. These form clear solutions and do not require filtration. The compositions of these formulas are given in Table II below:

TABLE II

| Tar Solution Component | Tar Solutions | | |
|---|---|---|---|
| | A % wt | B % wt | C % wt |
| Propylene glycol | 30 | 30 | 30 |
| SD Alcohol 40 | 32 | 32 | 32 |
| *Solulan-98 | 5 | 5 | 5 |
| Pine Tar | 2 | — | — |
| Juniper Tar | — | 2 | — |
| Liquor Carbonis Detergens | — | — | 2 |
| Demineralized Water | 31 | 31 | 31 |
| | 100 | 100 | 100 |

*Acetylated polyoxyethylene(10)lanolin ether

Using the tar solutions of Examples 1 to 3, the following gel preparations were made:

TABLE III

| Gel Components | Tar Gels | | |
|---|---|---|---|
| | A % wt | B % wt | C % wt |
| Tar Solution A | 97.25 | — | — |
| Tar Solution B | — | 97.25 | — |
| Tar Solution C | — | — | 97.25 |
| *WSP-X250 Protein | 0.75 | 0.75 | 0.75 |
| Carbopol 940 | 1.50 | 1.50 | 1.50 |
| Triethanolamine | 0.50 | 0.50 | 0.50 |
| | 100.00 | 100.00 | 100.00 |

*WSP-X250 Protein: Protein having a molecular weight of about 1000 prepared by the hydrolysis of animal collagen; Nitrogen - 8% min; Ash 2% Max; Moisture 45%; % N as amino nitrogen 10% min; isoelectric point 5.3; pH 5.8-6.3

A series of tar extracts were prepared starting with Crude Coal Tar USP. Sixty parts by weight of the solvent was mixed and heated with 40 parts by weight of the Crude Coal Tar at a temperature of about 160° T. Dicalite was then blended in and the mixture was filtered. The tar extract constituting the filtrate was collected and used in preparing the compositions. Table IV below summarizes the tar extracts which were prepared using the aforesaid procedure. Column 1 lists the solvents, the Crude Coal Tar and the Dicalite. The remaining columns indicate the percentage by weight of each of the particular solvents used in the extraction and the quantity of Crude Coal Tar and Dicalite. For the purposes of identification, the tar extracts are numbered Tar Extract No. 1 to Tar Extract No. 7. Thus, for example, Tar Extract No. 1 designates the extract prepared in accordance with the given procedure using 60% by weight of polyoxyethylene(10) oleyl ether and 40% by weight of Crude Coal Tar USP and Dicalite as required to facilitate the filtration of the extract.

TABLE IV

| Components mixed in Extraction | Tar Extract | | | | | | |
|---|---|---|---|---|---|---|---|
| | No. 1 %wt | No. 2 %wt | No. 3 %wt | No. 4 %wt | No. 5 %wt | No. 6 %wt | No. 7 %wt |
| Polyoxyethylene (10)oleyl ether | 60 | — | — | — | — | — | — |
| Isopropyl myristate | — | 60 | — | — | — | — | — |
| P.E.G.-300 dilaurate | — | — | 60 | — | — | — | — |
| Standamul-HE | — | — | — | 60 | — | — | — |
| Arlamol-E | — | — | — | — | 60 | — | — |
| Procetyl AWS | — | — | — | — | — | 60 | — |
| Polyoxyethylene (4)lauryl ether | — | — | — | — | — | — | 60 |
| Crude Coal Tar (USP) | 40 | 40 | 40 | 40 | 40 | 40 | 40 |
| *Dicalite | q.s. | q.s. | q.s. | q.s. | q.s. | q.s | q.s. |

*Dicalite - Diatomaceous Earth

The Tar Extracts of Table IV are used to prepare tar solutions. In preparing these solutions, propylene glycol, SA Alcohol 40 and Solulan 98 are thoroughly mixed. The Tar Extracts are then added to the solution so formed and mixing is continued for another 20-30 minutes. The resulting Tar Solution is then filtered. These Tar Solutions are summarized in Table V below:

TABLE V

| Tar Solution Components | Tar Solution | | | | | | |
|---|---|---|---|---|---|---|---|
| | No. 1 %wt | No. 2 %wt | No. 3 %wt | No. 4 %wt | No. 5 %wt | No. 6 %wt | No. 7 %wt |
| Propylene Glycol | 30 | 30 | 30 | 30 | 30 | 30 | 30 |
| SD Alcohol-40 | 32 | 32 | 32 | 32 | 32 | 32 | 32 |
| Solulan-98 | 5 | 5 | 5 | 5 | 5 | 5 | 5 |
| Tar Extract No. 1 | 2 | — | — | — | — | — | — |
| Tar Extract No. 2 | — | 2 | — | — | — | — | — |
| Tar Extract No. 3 | — | — | 2 | — | — | — | — |
| Tar Extract No. 4 | — | — | — | 2 | — | — | — |
| Tar Extract No. 5 | — | — | — | — | 2 | — | — |
| Tar Extract No. 6 | — | — | — | — | — | 2 | — |
| Tar Extract No. 7 | — | — | — | — | — | — | 2 |
| Demineralized Water | 31 | 31 | 31 | 31 | 31 | 31 | 31 |

The Tar Solutions described in Table V are used to prepare Tar Gel products. In preparing these products the Tar Solution and the Carbopol 940 are mixed until the latter is completely dispersed in the Tar Solution. The WSP-X250 Protein is added and then the triethanolamine is mixed in until a uniform gel forms. The Tar Gel products prepared in this fashion are summarized in Table VI below:

TABLE VI

| Tar Gel Components | Tar Gel | | | | | | |
|---|---|---|---|---|---|---|---|
| | No. 1 %wt | No. 2 %wt | No. 3 %wt | No. 4 %wt | No. 5 %wt | No. 6 %wt | No. 7 %wt |
| Tar Solution No. 1 | 97.25 | — | — | — | — | — | — |
| Tar Solution No. 2 | — | 97.25 | — | — | — | — | — |
| Tar Solution No. 3 | — | — | 97.25 | — | — | — | — |
| Tar Solution No. 4 | — | — | — | 97.25 | — | — | — |
| Tar Solution No. 5 | — | — | — | — | 97.25 | — | — |
| Tar Solution No. 6 | — | — | — | — | — | 97.25 | — |
| Tar Solution No. 7 | — | — | — | — | — | — | 97.25 |
| WSP-X250 Protein | 0.75 | 0.75 | 0.75 | 0.75 | 0.75 | 0.75 | 0.75 |
| Carbopol 940 | 1.50 | 1.50 | 1.50 | 1.50 | 1.50 | 1.50 | 1.50 |
| Triethanolamine | 0.50 | 0.50 | 0.50 | 0.50 | 0.50 | 0.50 | 0.50 |
| | 100.00 | 100.00 | 100.00 | 100.00 | 100.00 | 100.00 | 100.00 |

A further series of Tar Gel preparations were formulated which varied in the amount of propylene glycol and Tar Extract.

These are summarized in Table VII below:

TABLE VII

| Gel Components | Tar Gels | | | |
|---|---|---|---|---|
| | No. 8 | No. 9 | No. 10 | No. 11 |
| | %wt | %wt | %wt | %wt |
| Propylene glycol | 48.00 | 53.00 | 56.00 | 57.00 |
| SD Alcohol-40 | 39.85 | 30.85 | 30.85 | 30.85 |
| Demin. Water | 10.00 | 10.00 | 10.00 | 10.00 |
| Tar Extract No. 7 | 10.00 | 5.00 | 2.00 | 1.00 |
| Carbopol 940 | 1.00 | 1.00 | 1.00 | 1.00 |
| Triethanolamine | 0.15 | ;11 0.15 | 0.15 | 0.15 |

The procedure for preparing Tar Gels No. 8 to No. 11 is as follows:

Make a solution of the first three components. Disperse the Tar Extract into this solution with constant agitation for 20 to 30 minutes. Remove the mixer and allow mixture to set for 2 to 3 hours. Remove the supernatent liquid and pass it through a filter using vacuum. To the resulting filtrate add the Carbopol 940 slowly with constant agitation until complete solution is effected and it has thickened slightly. Finally, add the triethanolamine and mix thoroughly until gel is formed.

Another series of compositions encompassed by this invention were prepared using an auxiliary keralytic agent and a hydroxypropyl cellulose gelling agent. These are summarized in Table VIII below:

TABLE VIII

| Gel Components | Tar Gel | | | |
|---|---|---|---|---|
| | No. 12 | No. 13 | No. 14 | No. 15 |
| | %wt | %wt | %wt | %wt |
| Propylene glycol | 50.00 | 55.00 | 58.00 | 59.00 |
| SD Alcohol-40 | 22.00 | 22.00 | 22.00 | 22.00 |
| Demin. Water | 10.00 | 10.00 | 10.00 | 10.00 |
| Salicylic Acid | 6.00 | 6.00 | 6.00 | 6.00 |
| Tar Extract No. 7 | 10.00 | 5.00 | 2.00 | 1.00 |
| Klucel H.F. | 2.00 | 2.00 | 2.00 | 2.00 |

The Tar Gel No. 12 through No. 15 are prepared using the following procedure:

Make a solution of the first three components. Dissolve the salicylic acid in this solution with agitation. Then disperse the Tar Extract into this solution with constant agitation for 20 to 30 minutes. Remove the mixer and allow the mixture to set for 2 to 3 hours. Remove the supernatant liquid and pass it through a filter using vacuum. To the resulting filtrate add the Klucel H.F. slowly with constant agitation until complete solution is effected and the gel has formed.

Compositions of the present invention, and especially gel products, have been demonstrated to be superior to prior art commercial tar products both as to their substantivity to skin and as to their photodynamic properties. The former property is important to the utility of products of this kind in that it helps to insure that the products are longer lasting i.e. have a longer duration of activity. An increase in the latter property is important to the utility of these products since it increases the effectiveness of UV radiation given in the treatment of psoriasis. As pointed out above, one of the most effective treatments for psoriasis involves the application of a tar composition to the skin, followed by exposure to ultraviolet light which act synergistically. The tar sensitizes the skin making the UV radiation more effective. The degree of sensitization i.e. the photodynamism of the products can be evaluated by measuring the erythema that develops on the treated skin sites following the application of the product and exposure to UV light.

The Tar Gel No. 7 of this invention was tested against several commercial tar products and a few experimental products. These preparations may be described as follows:

Gel A: Allanton 2%; crude coal tar extract 5% versa-gel base in gel.

Lotion A: Actives of Gel A in lotion form.

Product Z: Shampoo containing crude colloidal coal 1%; allanton 0.2% and parachlorometoxylenol 0.5%.

Product IT: Shampoo containing 2% salicylic acid; tar, equipotent to 5% Liquor Carbonis Detergens; polyoxyethylene ethers; benzalkonium chloride 0.2%, alcohol 13%.

Product I: A shampoo composition containing ethoxylated ethers; 2.5% USP Coal Tar Solution; cationic polymer surfactant; .4% alcohol and benzalkonium chloride in non-ionic amphoteric base.

Product P: A shampoo containing Coal Tar Extract which is equivalent to 1% Crude Coal Tar.

T.D. Lotion: A lotion containing a Crude Coal Tar distillate.

Experimental Product No. 1: Hydrophyllic Ointment containing 5% Crude Coal Tar.

Experimental Product No. 2: Two percent by weight Tar Extract No. 7 disclosed in this application was mixed with the sodium salt of Carbopol 934 and then water was added to prepare a gel.

Experimental Product No. 3: Two Percent Crude Coal Tar was added to the sodium salt of Carbopol 934 and water was then added to prepare a gel.

Substantivity: The duration of activity and the relative strength of six tar-containing products were measured by determining the amount of fluorescence on human arms following a single application of the product. A measured amount of each material was applied to the arm, was allowed to remain on the skin for five minutes, and then was rinsed off and the skin blotted dry. Readings were taken at one hour post-application and daily thereafter for four days. Strength of fluorescence was recorded on a scale of 0 to 4 with 4 representing the maximum intensity. Tar Gel No. 7 demonstrated higher fluorescence readings at all times than any of the preparations tested. In fact, by 48 hours after application, Product Z was the only other product with visible fluorescence, and its reading (0.40) was substantially lower than that of Tar Gel No. 7 (1.85) of this invention. The data is summarized in Table IX below:

TABLE IX

Substantivity: Fluorescence on Human Skin (4=maximum)

| Product | Days Post-Application | | | | |
|---|---|---|---|---|---|
| | 0 (1 hr.) | 1 | 2 | 3 | 4 |
| Tar Gel No. 7 | 3.75 | 2.50 | 1.85 | 0.65 | 0.35 |
| Product Z | 2.80 | 1.35 | 0.40 | 0.15 | 0.10 |
| Product P | 3.00 | 0.35 | — | — | — |
| T.D. Lotion | 3.25 | 0.12 | — | — | — |
| Gel A | 1.30 | — | — | — | — |
| Lotion A | 1.30 | — | — | — | — |

Photodynamism in Guinea Pigs: The photodynamism (or phototoxicity) of tar-containing products in guinea pigs was evaluated by a measurement of erythema on treated sites following application of a measured amount of test agent and exposure of the treated sites to ultraviolet light (Westinghouse FS 40 lamp at a distance of 9 inches) for one hour. In preparation for this assay, the backs of the guinea pigs was shaved and depilated at least four hours prior to use, and duplicate applications was made to both sides of the back. Only one side of the back was exposed to UV light; the other side served as an unexposed control. Erythema on the test sites was measured 24 hours after UV exposure on a scale of 1 to 4, with 4 representing the maximum. The results of these studies are summarized in Table X below:

TABLE X

| Guinea Pig Photodynamism Assay (UVB) | |
|---|---|
| Product | Mean Erythema Reading (4=maximum) |
| Gel A | 3.00* |
| Lotion A | 3.00* |
| Tar Gel No. 7 | 2.75 |
| Product Z | 2.19 |
| Product I | 1.75 |
| T.D. Lotion | 1.57 |
| Product IT | 0.63 |
| Product P | 0.50 |

*Erythema was also observed on unexposed sites with this compound.

Tar Gel No. 7 of this invention had a greater photodynamic effect than all but two of the tested products, Gel A and Lotion A. It should be noted, however, that both the latter products were observed to produce erythema on the sites not exposed to UV (probably due to irritation), as well as on exposed sites. How much of the total erythemal response was due to the actual photodynamic effects of the two products, therefore, is not known. However, subtraction of the mean erythema seen on unexposed sites from the results of exposed sites would result in a reading of 2.75 for Gel A and 2.50 for Lotion A; the Tar Gel No. 7 reading was 2.75.

Photodynamism on Human Arms: The comparative photodynamism of nine tar-containing products was evaluated by measuring the erythema produced on sites treated with these products, blotted after five minutes, and then exposed to black light ultraviolet rays for slightly longer than one MED. Black light ultraviolet rays (UVA) were used because they have lower energy than short wave ultraviolet rays (UVB) and thus have less burning potential. As such, black light provides a more stringent test for the photodynamism of tar-containing products.

The degree of erythema on the test sites was measured on a scale of 0 to 4, with 4 representing maximum erythema. A period of 6 to 8 hours after UVA exposure was required to develop the maximum erythema response. Tar Gel No. 7 of this invention produced a greater phototoxic response than any of the other commercial compounds tested--a direct index of the effectiveness of tar-containing products--and it was equal to the standard of 5% crude coal tar in hydrophilic ointment. Table XI presents the complete data from this test.

TABLE XI

| Photodynamism on Human Arms with Black Light (UVA) | | |
|---|---|---|
| Compound | Mean Erythema Reading (4=maximum) | |
| Exp. Product No. 1 | 3.00 | (standard) |
| Tar Gel No. 7 | 3.00 | |
| Product Z | 2.00 | |
| T.D. Lotion | 0.38 | |
| Gel A | 0.00 | |
| Lotion A | 0.13 | |
| Product I | 0.00 | |
| Product IT | 0.00 | |
| Product P | 0.00 | |

Tar Gel No. 7 of this invention was compared also to three experimentally prepared formulations under conditions more likely to reduce its effect, and was found again to elicit a superior phototoxic effect on human arms. The compounds used for comparison were a Carbopol gel described in the literature (Am. J. Pharm., 1957, pp. 190-193) with 2% Tar Extract No. 7 incorporated, the same gel with 2% crude coal tar, and hydrophilic ointment with 5% crude coal tar. The test materials were applied to the subjects' arms, washed off after one hour rather than just blotted, and the arms then were exposed to black light ultraviolet rays 24 hours later. As Table XII below shows, Tar Gel No. 7 of this invention produced a greater mean phototoxic response than any of the others. It is especially significant that Tar Gel No. 7 was more effective in this test than 5% crude coal tar in hydrophilic ointment, which is used in most hospital and clinic programs of tar/UV therapy for psoriatics.

TABLE XII

| Photodynamism on Human Arms, with Black Light (UVA) 24 Hours after Application (maximum erythema=4) | | | | |
|---|---|---|---|---|
| Subject | Tar Gel No. 7 | Exp. Product No. 1 | Exp. Product No. 2 | Exp. Product No. 3 |
| 1 | 0 | 0 | 0 | 0 |
| 2 | 3 | 2 | 0 | 0 |
| 3 | 1 | 0 | 0 | 0 |
| 4 | 2 | 2.5 | 2 | 0 |
| 5 | 0 | 0 | 0 | 0 |
| Mean | 1.2 | 0.9 | 0.4 | 0 |

Dosage and Administration

Psoriasis

As a replacement for other, less convenient and acceptable tar preparations, the compositions of this invention can be applied at bedtime in the following manner: the patient should message the composition into affected areas, allow it to remain for 5 minutes, and then remove excess by patting dry with tissues. This procedure minimizes staining of skin and clothing, leaving behind an almost invisible layer of the active tar. If any staining of fabric should occur, it can be removed easily by standard laundry procedures.

The superior substantivity of the present compositions makes it possible for the patient undergoing tar-/UV therapy to apply the gel at bedtime and report for UV treatment anytime the next day.

Chronic atopic dermatitis, Lichen simplex chronicus, and Nummular eczema

Apply twice daily as described above.

More than two applications per day are not recommended in the treatment of any of the indicated conditions, due to high skin substantivity of the present products, as shown in the above studies.

What is claimed is:

1. A therapeutic aqueous gel composition suitable for treating skin comprising:
    (a) from about 1 to about 10% by weight of an organic solvent extract of Crude Coal Tar;
    (b) from about 25% to about 65% by weight of propylene glycol;
    (c) from about 20% to about 35% by weight of ethyl alcohol;
    (d) from about 0.5% to about 5% by weight of a gelling agent; and (e) from about 5% to 35% water; said gelling agent being a neutralized carboxyl interpolymer of a monomeric monoolefinic acrylic acid of the structure:

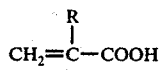

where R is a substituent selected from the class consisting of hydrogen and lower alkyl groups, and from about 0.1 to about 10% by weight based on the total monomers of a monomeric polyether of an oligosaccharide in which the hydroxyl groups which are modified are etherified with allyl groups, said polyether containing at least two allyl ether groups per oligosaccharide molecule and said interpolymer having a molecular weight of the order of about 1,000,000.

2. A composition according to claim 1 in which said organic solvent is selected from the group consisting of isopropyl myristate; PEG-6-dilaurate; polyoxyethylene(4) lauryl ether; propoxylated (15 moles propylene oxide)stearyl ether; polyoxyethylene(10) oleyl ether; polypropylene glycol(5) cetyl ether and glycereth-7-coconate.

3. A composition according to claim 2 wherein the extract is formed from 60% by weight of solvent and 40% by weight of Crude Coal Tar.

4. A composition according to claim 1 including a keralytic agent.

5. A composition according to claim 4 in which the keralytic agent is salicylic acid.

6. A composition according to claim 1 including a protein.

7. A composition according to claim 1 including an emulsifying agent.

8. A composition according to claim 1 in which said organic solvent extract of Crude Coal Tar is present in the amount of about 2% by weight.

9. A composition according to claim 1 in which said organic solvent extract of Crude Coal Tar, said propylene glycol, said alcohol and said water constitute a composite tar solution making up about 97.25% by weight of said total composition; said propylene glycol comprising about 30% by weight of said composite tar solution and said alcohol comprisng about 32% by weight of said composite tar solution.

10. A method for treating psoriasis which comprises applying to the effected skin area a therapeutically effective amount of the composition of claim 1, permitting said composition to remain on said affected skin area for about 5 minutes and then removing any excess of material.

11. The method of claim 10 including the additional step of exposing the skin area to which said composition has been applid to UV radiation.

12. A method for treating chronic atopic dermatitis, lichen simplex chronicus or nummular eczema which comprises applying to the effected skin area a therapeutically effective amount of the composition of claim 1 permitting said composition to remain on said effected skin area for about 5 minutes and then removing the excess of material.

* * * * *

UNITED STATES PATENT AND TRADEMARK OFFICE
CERTIFICATE OF CORRECTION

PATENT NO. : 4,102,995
DATED : July 25, 1978
INVENTOR(S) : PETER HEBBORN

It is certified that error appears in the above-identified patent and that said Letters Patent are hereby corrected as shown below:

Column 7, Table VII, under No. 8, delete "39.85"

and substitute therefor -- 30.85 --

Column 7, Table VII, under No. 9, delete ";110.15"

and substitute therefor -- 0.15 --

Signed and Sealed this

Thirtieth Day of January 1979

[SEAL]

Attest:

RUTH C. MASON
Attesting Officer

DONALD W. BANNER
Commissioner of Patents and Trademarks